US010364302B2

(12) United States Patent
Joung et al.

(10) Patent No.: US 10,364,302 B2
(45) Date of Patent: Jul. 30, 2019

(54) GROUP 4 TRANSITION METAL COMPOUND AND USE THEREOF

(71) Applicant: HANWHA CHEMICAL CORPORATION, Seoul (KR)

(72) Inventors: Ui Gab Joung, Daejeon (KR); Kil Sagong, Daejeon (KR); Sung Hae Jun, Gyeonggi-do (KR); Dong Ok Kim, Seoul (KR); Hye Ran Park, Gyeongsangbuk-do (KR); In Jun Lee, Gyeonggi-do (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 4 days.

(21) Appl. No.: 15/536,553

(22) PCT Filed: Dec. 23, 2015

(86) PCT No.: PCT/KR2015/014184
§ 371 (c)(1),
(2) Date: Jun. 15, 2017

(87) PCT Pub. No.: WO2016/105122
PCT Pub. Date: Jun. 30, 2016

(65) Prior Publication Data
US 2018/0002461 A1    Jan. 4, 2018

(30) Foreign Application Priority Data

Dec. 23, 2014    (KR) .......................... 10-2014-0187189

(51) Int. Cl.
*C08F 4/76*      (2006.01)
*C08F 4/64*      (2006.01)
(Continued)

(52) U.S. Cl.
CPC ............ *C08F 4/64044* (2013.01); *C07F 7/00* (2013.01); *C08F 4/64* (2013.01); *C08F 297/08* (2013.01)

(58) Field of Classification Search
CPC ........................ C08F 4/60072; C08F 4/64072
See application file for complete search history.

(56) References Cited

U.S. PATENT DOCUMENTS 6,255,419 B1 *  7/2001  Imuta ...................... C08F 12/04
                                                    502/104
2012/0012821 A1   1/2012  Langer et al.

FOREIGN PATENT DOCUMENTS

EP    3187499 A1    7/2017
EP    3239157 A1   11/2017
(Continued)

OTHER PUBLICATIONS

Hwang, E.Y.; Park, G.H.; Lee, C.S.; Kang, Y.Y.; Lee, J.; Lee, B.Y. Dalton Trans., 2015, 44, 3845-3855. (Year: 2015).*
(Continued)

*Primary Examiner* — Rip A Lee
(74) *Attorney, Agent, or Firm* — Marshall, Gerstein & Borun LLP

(57) ABSTRACT

The present invention relates to a novel Group 4 transition metal compound, a method for preparing the compound, a catalyst composition comprising the compound, and a method for preparing a polyolefin comprising performing a polymerization reaction of olefin monomers, in the presence of the catalyst composition. Since the Group 4 transition metal compound of the present invention exhibits an excellent catalytic activity in polyolefin synthesis reactions, as well as having excellent thermal stability, it can be used for polyolefin synthesis reactions at high temperatures, and by changing the type of a central metal and ligand, the weight average molecular weight of synthesized polyolefins and the
(Continued)

octene content in the polymer can be controlled. Therefore, it can be effectively used in polyolefin synthesis processes in which grades are controlled.

20 Claims, 1 Drawing Sheet

(51) Int. Cl.
  *C07F 7/00* (2006.01)
  *C08F 297/08* (2006.01)

(56) References Cited

FOREIGN PATENT DOCUMENTS

| JP | 10-081708 A | * | 3/1998 | ............. C08F 4/642 |
|---|---|---|---|---|
| KR | 2008-0000355 A | | 1/2008 | |
| KR | 2014-0121343 A | | 10/2014 | |
| WO | WO-2010-079051 A1 | | 7/2010 | |

OTHER PUBLICATIONS

Tabernero, V.; Cuenca, T.; Mosquera, M.E.G.; de Arellano, C.R. Polyhedron 2009, 28, 2545-2554. (Year: 2009).*
Ketterer, N.A.; Ziller, J.W.; Rheingold, A.L.; Heyduk, A.F. Organometallics 2007, 26, 5330-5338. (Year: 2007).*
Dorado, I.; Garces, A.; Lopez-Mardomingo, C.; Fajardo, M.; Rodriguez, A.; Antinolo, A.; Otero, A. Dalton 2000, 14, 2375-2382. (Year: 2000).*
Office Action, Korean Patent Application No. 10-2014-0187189, dated Jan. 19, 2018.
V. Tabernero et al., Studies of Nature of the Catalytic in the α-Olefin Polymerisation Processes, Eur. J. Inorg. Chem 2005, 338-346, © 2005 Wiliey-VCH Verlag Gmbh & Co. KGaA, Weinheim.
International Preliminary Report on Patentability for International Application No. PCT/KR2015/014184, dated Jun. 27, 2017.
Chaudhry, S. C. et al., Proceedings of the National Academy of Sciences, India, vol. 75, A, Part 1, pp. 11-15, Mar. 2005.
Malhotra, K. C. et al., Acceptor Properties of Titanium 2-Naphthyloxides, vol. 3, No. 1, pp. 125-128 (1984).
Hwang, Eun Yeong et al., Preparation of octahydro- and tetrahydro-[1,10]phenanthroline zirconium and hafniumcomplexes for olefin polymerization, Dalton Transactions, vol. 44, pp. 3845-3855 (2015).
Boussie et al., Journal of the American Chemical Society Articles, 2003, vol. 125: pp. 4306-4317.
International Search Report for International Application No. PCT/KR2015/014184, dated Apr. 1, 2016.
Supplemental European Search Report for Application No. 15873649.6, dated Aug. 20, 2018.
Tabernero et al, "Early transition metal derivatives stabilized by the phenylenediamido 1,2,-C6H4(NCH2tBu)2 ligand: Synthesis, characterization and reactivity studies: Crystal structures of [Ta{1,2,-C6H4(NCH2tBu)2}2Cl] and [ZR{1,2,-C6H4(NCH2tBu)2}(NMe2)μ-NMe2)]2," *Polyhedrown*, 28:2545-2554 (2009).
Ketterer et al, "Imido and Organometallic-Amido Titanium (IV) Complexes of a Chelating Phenanthrenediamide Ligand," *Organometallics*, 26:5330-5338 (2007).
Dorado et al., "Synthesis and structural characterization of new organo-diimido and organo-imido niobium and titanium complexes," Database CA, Chemical Abstracts Service, Columbus, Ohio US 2000, XP002783672, Retrieved from STN Database accession No. 2000:464493.
Jun et al., "Preparation of Phosphine-Amido Hafnium and Zirconium Complexes for Olefin Polymerization," *Organometallic*, 32(24):7357-7365 (2013).
Notice of Allowance for Korean Application No. 10-2014-0187189, dated Aug. 25, 2018.

* cited by examiner

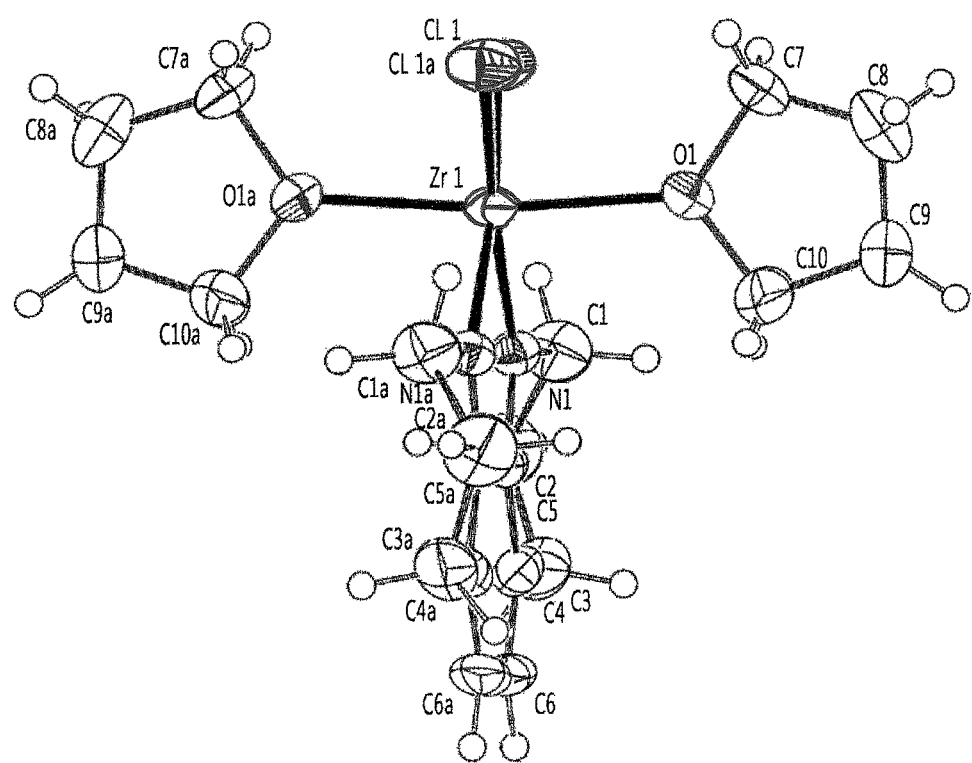

GROUP 4 TRANSITION METAL COMPOUND AND USE THEREOF

CROSS REFERENCE TO RELATED APPLICATIONS

This application is the U.S. National Phase of International Application No. PCT/KR2015/014184 filed Dec. 23, 2015 which claims the benefit of Korean Patent Application No. 10-2014-0187189 filed Dec. 23, 2014.

BACKGROUND

Technical Field

The present invention relates to a novel Group 4 transition metal compound, a method for preparing the compound, a catalyst composition comprising the compound, and a method for preparing a polyolefin comprising performing a polymerization reaction of olefin monomers, in the presence of the catalyst composition.

Background Art

Polyolefins are used as raw materials for manufacturing various products used in daily life, such as shopping bags, greenhouses, fishing nets, packaging materials for cigarettes, ramen pouches, yogurt bottles, battery cases, automobile bumpers, interior materials, shoe soles, washing machines, etc.

Conventional olefin polymers and copolymers such as ethylene polymers, propylene polymers, and ethylene-alpha-olefin copolymers have been prepared by heterogeneous catalysts composed of titanium compounds and alkylaluminum compounds. Recently, metallocene catalysts, which are homogeneous catalysts having an extremely high catalytic activity, have been developed, and methods for preparing a polyolefin using a metallocene catalyst have been studied.

Although metallocene catalysts were already reported in the 1950s, their activity was too low to continue studies thereon. After Professor Kaminsky of Germany first reported in 1976 that methylaluminoxane could be used as a cocatalyst to exhibit a high activity, research on metallocene catalysts was accelerated. Initial single-active-site homogeneous catalysts were in the form of a metallocene compound of a Group 4 metal coordinated by two cyclopentadienyl ligands activated by methylaluminoxane (MAO). Thereafter, it was expanded to the "half-metallocene" catalyst form represented by Dow's constrained geometry catalyst (CGC), and this form of catalysts exhibited more excellent properties in copolymerization than the initial metallocene catalysts. This has been expanding in the form of "post-metallocene" catalysts that do not contain cyclopentadienyl ligands since the beginning of 2000. Most single-active-site catalysts have a similar structure of "$LMX_2$". In particular, M is a central metal, L is a spectator ligand which is always coordinated to the metal, X is an acting ligand composed of a halogen atom, alkyl group, etc., one of which is desorbed as an anion by a cocatalyst to make the central metal as a cation, and a polymer chain grows from the other X.

In the early 2000s, Dow and Symyx jointly utilized high-throughput-screening (HTS) technology to report a new type of a catalyst (*Journal of the American Chemical Society*, 2003, 125: 4306). The catalyst has the structure of "$LMX_3$" and is distinguished from conventionally-known catalysts having the structure of "$LMX_2$". The catalyst of Dow and Symyx is characterized in that the spectator ligand L is in the form of an ether-amido chelate. Thereafter, catalysts having the structure of "$LMX_3$" in which the spectator ligand L is diversified into imine-amido, imine-enamido, aminotropone-iminate, etc. were additionally developed.

However, among the developed catalysts described above, few are commercially applied, and the discovery of a catalyst, which exhibits a high activity even at a high temperature of 100° C. or higher, has thermal stability, and exhibits more improved polymerization performance capable of preparing polyolefins of various grades by changing the structures of its central metal and ligand, is still required.

SUMMARY

An object of the present invention is to provide a novel Group 4 transition metal compound.

Another object of the present invention is to provide a method for preparing the Group 4 transition metal compound.

A further object of the present invention is to provide a catalyst composition comprising the Group 4 transition metal compound.

A still further object of the present invention is to provide a method for preparing a polyolefin comprising performing a polymerization reaction of olefin monomers, in the presence of the catalyst composition comprising the Group 4 transition metal compound.

BRIEF DESCRIPTION OF THE DRAWINGS

FIG. 1 is a diagram illustrating an X-ray diffraction crystal structure of the compound represented by Formula 1-9 comprising zirconium as a central metal according to an exemplary embodiment of the present invention.

DETAILED DESCRIPTION

In an aspect to achieve the above objects, the present invention provides a Group 4 transition metal compound represented by Formula 1 below:

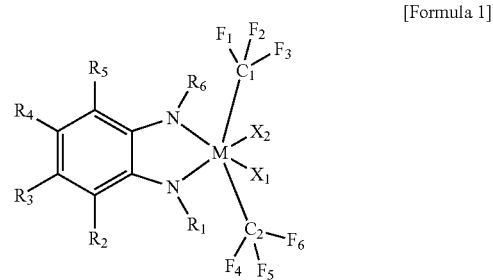

[Formula 1]

wherein, in Formula 1, M is a Group 4 transition metal of Ti, Zr, Hf, or Rf;

each of $X_1$ and $X_2$ is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene;

each of $R_1$ to $R_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or $R_1$ and $R_2$, $R_2$ and $R_3$, $R_4$ and $R_5$, or $R_5$ and $R_6$ are linked together to form a substituted or unsubstituted $C_{5-14}$ ring, wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene;

each of C1 and C2 is independently an element of Group 5 or Group 6 of the Periodic Table; and each of $F_1$ to $F_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or any two of $F_1$ to $F_3$ or any two of $F_4$ to $F_6$ are linked together to form a substituted or unsubstituted $C_{5-14}$ ring comprising or not comprising a heteroelement, wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

As used herein, the term "substitution" may mean that a hydrogen atom is replaced with a functional group such as another atom or atomic group, unless otherwise specified.

In the present invention, alkyl, alkenyl, and alkynyl may be linear, branched, or cyclic.

The present invention provides a Group 4 transition metal compound of a novel structure in which a ligand in the form of a phenanthroline-like chelate is coordinated. As described above, conventional single-active-site homogeneous catalysts have been mainly developed as coordination entities of ligands based on carbon, nitrogen, and oxygen atoms, such as cyclopentadienyl, amido, phenoxo, amine, imine, ether, etc. Recently, a coordination entity of a ligand based on quinoline has been reported, but its structure differs from that of the compound of the present invention, and a bidentate coordination entity based on phenanthroline has not been reported.

Preferably, the above-mentioned novel Group 4 transition metal compound may be a Group 4 transition metal compound represented by Formula 2 below:

[Formula 2]

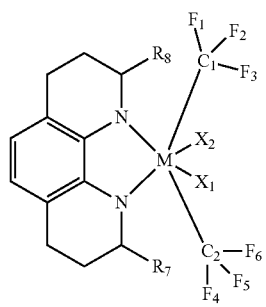

wherein, in Formula 2, M, $X_1$, $X_2$, $C_1$, $C_2$, and $F_1$ to $F_6$ are the same as defined above, and each of $R_7$ and $R_8$ is independently hydrogen, or substituted or unsubstituted $C_{1-20}$ alkyl.

Each of the $X_1$ and $X_2$ may be independently halogen. Preferably, $X_1$ and $X_2$ may be both chlorine, but are not limited thereto.

Preferably, each of $R_7$ and $R_8$ may be identical to or different from each other, and may be independently hydrogen, methyl, ethyl, isopropyl, butyl, or phenyl, but is not limited thereto.

Further, preferably, $C_1$ and $C_2$ may be both nitrogen or both oxygen, but are not limited thereto.

In particular, each of $F_1$ to $F_6$ may be independently absent, hydrogen, or methyl.

More preferably, i) when $C_1$ and $C_2$ are both nitrogen, any one of $F_1$ to $F_3$ and any one of $F_4$ to $F_6$ are hydrogen, the remaining two may be both methyl, respectively, ii) when $C_1$ and $C_2$ are both oxygen, any one of $F_1$ to $F_3$ and any one of $F_4$ to $F_6$ are absent, and the remaining two may be linked together to form a tetrahydrofuran ring by comprising the oxygen, respectively, but the present invention is not limited thereto.

Non-limiting examples of the compound include Group 4 transition metal compounds represented by the formulas selected from the group consisting of

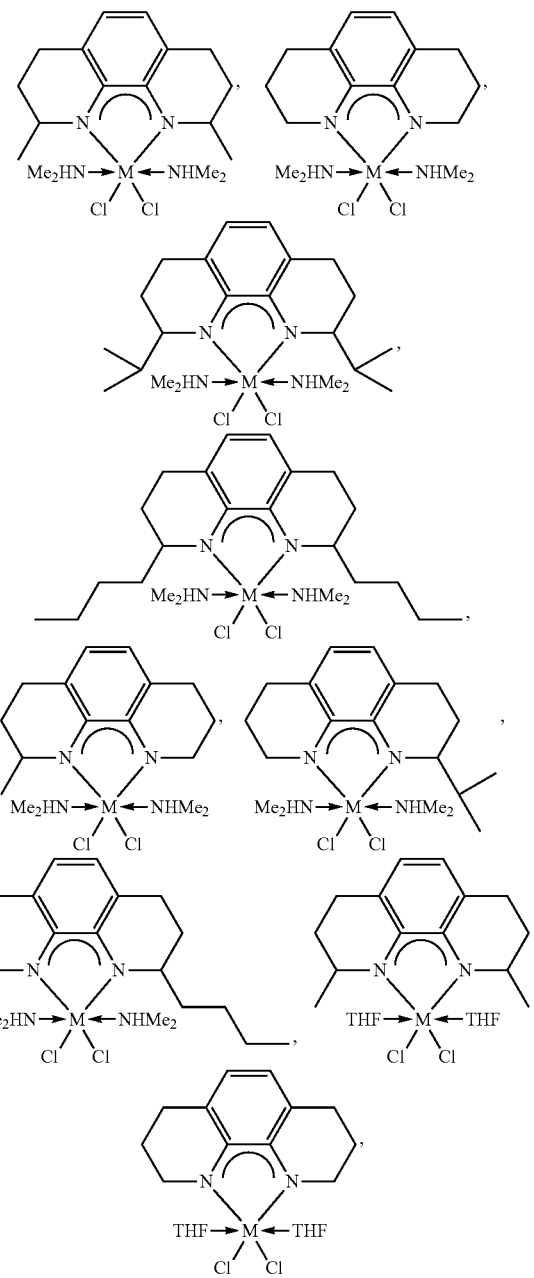

-continued

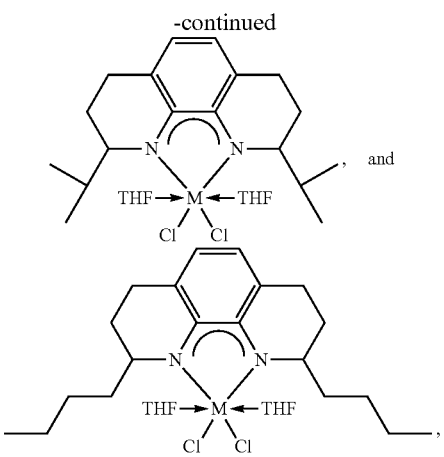

wherein, in the above formulas, M is a Group 4 transition metal of Ti, Zr, Hf, or Rf; A is aluminum or boron; Me is methyl; and THF is tetrahydrofuran.

In another aspect, the present invention provides a method for preparing a compound represented by Formula 1 below, comprising reacting a compound represented by Formula 3 below and a compound represented by Formula 4 below:

[Formula 1]

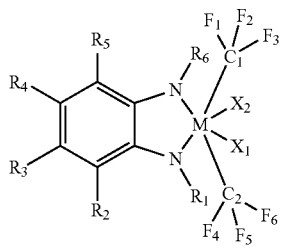

[Formula 3]

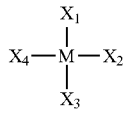

[Formula 4]

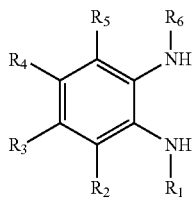

wherein, in the above formulas, M, $R_1$ to $R_6$, $X_1$ to $X_3$, $C_1$, $C_2$, and $F_1$ to $F_6$ are the same as defined above, and $X_4$ is halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

The compound represented by Formula 4 may be a phenanthroline derivative. The phenanthroline derivative can be used by purchasing commercial products or by preparation according to synthesis methods known in the art. For example, known synthesis methods by Dr. Qing-Hua Fan (*Angew. Chem. Int. Ed.*, 2013, 52: 7172-7176), Dr. Liang-jie Yuan (*Cryst Eng Comm*, 2013, 15: 1414), Dr. Francesco Vizza (*Inorganica Chimica Acta*, 2008, 361: 3677), etc., may be referenced for synthesis, but the methods are not limited thereto. Non-limiting examples of the compound represented by Formula 4 that can be used for preparing the Group 4 transition metal compound of the present invention may include 1,2,3,4,7,8,9,10-octahydro-1,10-phenanthroline, 2,9-dimethyl-1,2,3,4,7,8,9,10-octahydro-1,10-phenanthroline, 2,9-diisopropyl-1,2,3,4,7,8,9,10-octahydro-1,10-phenanthroline, 2,9-dibutyl-1,2,3,4,7,8,9,10-octahydro-1,10-phenanthroline, 9-butyl-2-ethyl-1,2,3,4,7,8,9,10-octahydro-1,10-phenanthroline, 2,9-diphenyl-1,2,3,4,7,8,9,10-octahydro-1,10-phenanthroline, 9-butyl-2-methyl-1,2,3,4,7,8,9,10-octahydro-1,10-phenanthroline, 9-methyl-1,2,3,4,7,8,9,10-octahydro-1,10-phenanthroline, 9-butyl-1,2,3,4,7,8,9,10-octahydro-1,10-phenanthroline, 9-isopropyl-1,2,3,4,7,8,9,10-octahydro-1,10-phenanthroline, 2-butyl-1,2,3,4,7,8,9,10-octahydro-1,10-phenanthroline, 2-isopropyl-1,2,3,4,7,8,9,10-octahydro-1,10-phenanthroline, 2-methyl-1,2,3,4,7,8,9,10-octahydro-1,10-phenanthroline, 2-phenyl-1,2,3,4,7,8,9,10-octahydro-1,10-phenanthroline, 9-phenyl-1,2,3,4,7,8,9,10-octahydro-1,10-phenanthroline, 2-butyl-9-methyl-1,2,3,4,7,8,9,10-octahydro-1,10-phenanthroline, 2-butyl-9-isopropyl-1,2,3,4,7,8,9,10-octahydro-1,10-phenanthroline, and 2-butyl-9-ethyl-1,2,3,4,7,8,9,10-octahydro-1,10-phenanthroline.

Preferably, the compound represented by Formula 4 may be a 1,2,3,4,7,8,9,10-octahydro-1,10-phenanthroline derivative, but is not limited thereto.

In the reaction above, preferably, the compound represented by Formula 3 and the compound represented by Formula 4 may be reacted at an equivalent ratio of 1:0.9 to 1:1.5, but the equivalent ratio is not limited thereto.

Further, preferably, the reaction may be performed in a hydrocarbon solvent selected from the group consisting of $C_{5-10}$ aliphatic or aromatic hydrocarbon, $C_{1-10}$ saturated or unsaturated hydrocarbon unsubstituted or substituted with halogen atoms, and a mixture thereof. More preferably, the hydrocarbon solvent may be toluene, pentane, hexane, heptane, cyclohexane, methylcyclohexane, benzene, xylene, dichloromethane, chloroethane, dichloroethane, chlorobenzene, or a mixture thereof, but is not limited thereto.

In particular, the hydrocarbon solvent may be used in an amount of 100 parts by weight to 1000 parts by weight based on 100 parts by weight of the sum of the compound represented by Formula 3 and the compound represented by Formula 4, but is not limited thereto.

Preferably, the reaction may be performed at 0° C. to 100° C., and may be performed for 30 minutes to 30 hours, but is not limited thereto.

In a specific exemplary embodiment of the present invention, a Group 4 transition metal organic compound (M=Ti, Zr, Hf, or Rf) such as $M(NMe_2)_2Cl_2(dme)$ or $Zr(CH_2Ph)_2 Cl_2(Et_2O)_{0.2}$, etc., as the compound represented by Formula 3, and a 1,2,3,4,7,8,9,10-octahydro-1,10-phenanthroline derivative as the compound represented by Formula 4 were added together in a hydrocarbon solvent such as toluene, etc., and reacted with or without a small amount of tetrahydrofuran, by stirring at 0° C. to 100° C., for example, at 20° C. to 30° C., for 30 minutes to 30 hours in a reactor. By performing the reaction under the above-mentioned conditions, the transition metal compound can be obtained at a higher yield, but the reaction conditions are not limited thereto, and the reaction conditions can be appropriately controlled depending on the type of the two compounds and/or the combination with the solvent.

Furthermore, after the reaction is completed, the preparation method may additionally be followed by conventional post-treatment processes, for example, removal of a solvent and unreacted compounds, and washing and drying of the product. The removal of the solvent may be performed by evaporation under reduced pressure using a vacuum pump, etc., but the removal method is not limited thereto.

In another aspect, the present invention provides a catalyst composition, comprising:

a Group 4 transition metal compound; and at least one compound selected from the group consisting of a compound represented by Formula 5 below, a compound represented by Formula 6 below, and a compound represented by Formula 7 or Formula 8 below:

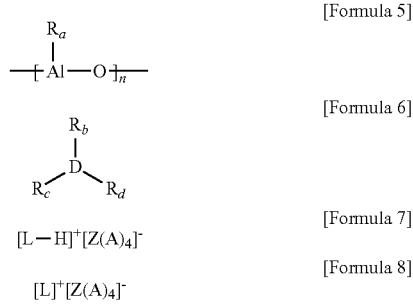

[Formula 5]

[Formula 6]

[L−H]$^+$[Z(A)$_4$]$^−$ [Formula 7]

[L]$^+$[Z(A)$_4$]$^−$ [Formula 8]

wherein, in the formulas, $R_a$ is hydrogen, halogen, $C_{1-20}$ alkyl unsubstituted or substituted with halogen, $C_{3-20}$ cycloalkyl unsubstituted or substituted with halogen, $C_{6-40}$ aryl unsubstituted or substituted with halogen, or $C_{6-40}$ alkylaryl unsubstituted or substituted with halogen;

n is an integer of 2 or greater;

D is aluminum or boron;

each of $R_b$ to $R_d$ is identical to or different from each another, and is independently a hydrogen atom, halogen, $C_{1-20}$ alkyl unsubstituted or substituted with halogen, $C_{3-20}$ cycloalkyl unsubstituted or substituted with halogen, $C_{1-20}$ alkoxy, $C_{6-40}$ aryl unsubstituted or substituted with halogen, $C_{6-40}$ alkylaryl, or $C_{6-40}$ arylalkyl unsubstituted or substituted with halogen;

L is a neutral or cationic Lewis acid;

Z is a Group 13 element; and

A is substituted or unsubstituted $C_{6-20}$ aryl or substituted or unsubstituted $C_{1-20}$ alkyl.

Preferably, the catalyst composition may comprise the compound represented by Formula 5, the compound represented by Formula 6, or a mixture thereof; and the compound represented by Formula 7 or Formula 8.

Preferably, the catalyst composition of the present invention may comprise the compound represented by Formula 1; the compound represented by Formula 5, the compound represented by Formula 6, or a mixture thereof, and the compound represented by Formula 7 or Formula 8, at a molar ratio of 1:1 to 5:20 to 500.

The compound represented by Formula 5 is aluminoxane, and may preferably be alkylaluminoxane. Non-limiting examples of the aluminoxane may include methylaluminoxane, ethylaluminoxane, isobutylaluminoxane, butylaluminoxane, etc., and preferably, methylaluminoxane can be used, but are not limited thereto. The alkylaluminoxane to be used may be prepared by adding an appropriate amount of water to trialkylaluminum or by reacting a hydrocarbon compound containing water or an inorganic hydrate salt with trialkylaluminum, etc., but is not limited thereto, and commercially available alkylaluminoxanes can be purchased for use. When alkylaluminoxane is prepared by conventional preparation methods, generally, linear and cyclic aluminoxane can be obtained in a mixed form.

The compound represented by Formula 6 above may preferably be an organic compound comprising a Group 13 metal, for example, aluminum or boron. In Formula 7 above, the three substituents are identical to or different from each another. Non-limiting examples of the compound represented by Formula 7 include trimethylaluminum, dimethyl aluminum chloride, methoxydimethylaluminum, methylaluminum dichloride, triethylaluminum, diethylaluminum chloride, methoxydiethylaluminum, ethylaluminum dichloride, tripropylaluminum, dipropylaluminum chloride, propylaluminum dichloride, triisopropyl aluminum, tributylaluminum, triisobutylaluminum, diisobutylaluminum hydride, tricyclopentylaluminum, tripentylaluminum, triisopentylaluminum, trihexylaluminum, trioctylaluminum, ethyldimethylaluminum, diethyl(methyl)aluminum, triphenylaluminum, tri-p-tolylaluminum, ethoxydimethylaluminum, trimethylboron, triethylboron, triisobutylboron, tripropylboron, tributylboron, tripentafluorophenylboron, etc.

Non-limiting examples of the compound represented by Formula 7 or Formula 8 may include methyldioctadecylammonium tetrakis(pentafluorophenyl)borate ([HNMe$(C_{18}H_{37})_2$]$^+$[B$(C_6F_5)_4$]$^−$), trimethylammonium tetrakis(phenyl)borate, triethylammonium tetrakis(phenyl)borate, tripropylammonium tetrakis(phenyl)borate, tributylammonium tetrakis(phenyl)borate, trimethylammonium tetrakis(p-tolyl)borate, tripropylammonium tetrakis(p-tolyl)borate, trimethylammonium tetrakis(o,p-dimethylphenyl)borate, triethylammonium tetrakis(o,p-dimethylphenyl)borate, trimethylammonium tetrakis(p-trifluoromethylphenyl)borate, tributylammonium tetrakis(p-trifluoromethylphenyl)borate, tributylammonium tetrakis(pentafluorophenyl)borate, diethylammonium tetrakis(pentafluorophenyl)borate, triphenylphosphonium tetrakis(phenyl)borate, trimethylphosphonium tetrakis(phenyl)borate, N,N-diethylanilinium tetrakis(phenyl)borate, N,N-dimethylanilinium tetrakis(pentafluorophenyl)borate, N,N-diethylanilinium tetrakis(pentafluorophenyl)borate, triphenylcarbonium tetrakis(p-trifluoromethylphenyl)borate, triphenylcarbonium tetrakis(pentafluorophenyl)borate, trimethylammonium tetrakis(phenyl)aluminate, triethylammonium tetrakis(phenyl)aluminate, tripropylammonium tetrakis(phenyl)aluminate, tributylammonium tetrakis(phenyl)aluminate, trimethylammonium tetrakis(p-tolyl)aluminate, tripropylammonium tetrakis(p-tolyl)aluminate, triethylammonium tetrakis(o,p-dimethylphenyl)aluminate, tributylammonium tetrakis(p-trifluoromethylphenyl)aluminate, trimethylammonium tetrakis(p-trifluoromethylphenyl)aluminate, tributylammonium tetrakis(pentafluorophenyl)aluminate, N,N-diethylanilinium tetrakis(phenyl)aluminate, N,N-dimethylanilinium tetrakis(phenyl)aluminate, N,N-diethylanilinium tetrakis(pentafluorophenyl)aluminate, diethylammonium tetrakis(pentafluorophenyl)aluminate, triphenylphosphonium tetrakis(phenyl)aluminate, trimethylphosphonium tetrakis(phenyl)aluminate, triethylammonium tetrakis(phenyl)aluminate, tributylammonium tetrakis(phenyl)aluminate, etc., but are not limited thereto. Preferably, methyldioctadecylammonium tetrakis(pentafluorophenyl)borate ([HNMe$(C_{18}H_{37})_2$]$^+$[B$(C_6F_5)_4$]$^−$), N,N-dimethylanilinium tetrakis(pentafluorophenyl)borate, triphenylcarbonium tetrakis(pentafluorophenyl)borate, etc., may be used.

The catalyst composition of the present invention can be prepared by mixing the Group 4 transition metal compound of the present invention and the above-exemplified cocatalyst compound to be in contact with each other. The mixing can be performed under an inert gas atmosphere such as nitrogen or argon without a solvent or in the presence of a hydrocarbon solvent. For example, the mixing can be performed at 0° C. to 100° C., preferably at 10° C. to 30° C. After preparation in a hydrocarbon solvent, etc., the catalyst composition in a uniformly dissolved solution state may be used as is, or it may be used after converting it into a solid powder state by removing the solvent. The catalyst composition in the solid powder state may be obtained by precipitating the catalyst composition in a solution state followed by the solidification of the precipitate. Further, the catalyst composition of the present invention can be used in a form in which a Group 4 transition metal compound and a cocatalyst compound are supported in a carrier such as silica, alumina, or a mixture thereof, or an insoluble particle form of the carrier, but the form of the catalyst composition is not limited thereto.

In a specific exemplary embodiment of the present invention, the cocatalyst compound may comprise a compound represented by Formula 5, a compound represented by Formula 6, a compound represented by Formula 7 or Formula 8, or two or more compounds selected therefrom together. For example, methylaluminoxane, which is a compound represented by Formula 5, and methyldioctadecylammonium tetrakis(pentafluorophenyl)borate ([HNMe$(C_{18}H_{37})_2]^+[B(C_6F_5)_4]^-$), which is a compound represented by Formula 7, were mixed and used. In particular, the catalyst composition can be prepared by sequentially adding and mixing the compound represented by Formula 7 or Formula 8, the compound represented by Formula 5, and/or the compound represented by Formula 6 into a transition metal compound solution which is dissolved in a hydrocarbon solvent. In order to provide a catalyst composition exhibiting a high activity in polyolefin synthesis, the transition metal compound used, the compound represented by Formula 5, and/or the compound represented by Formula 6, and the compound represented by Formula 7 or 8 may be used at the above-mentioned ratio, that is, at a molar ratio of 1:1 to 5:20 to 500. More preferably, they may be used at a molar ratio of 1:1 to 2:100 to 200, but the molar ratio is not limited thereto.

In another aspect, the present invention provides a method for preparing a polyolefin, comprising performing a polymerization reaction of olefin monomers, in the presence of the catalyst composition.

The preparation method of a polyolefin according to the present invention can be achieved through contacting the catalyst composition with two or more molecules of olefin monomers.

In addition, as described above, since the catalyst composition of the present invention can exist not only in a uniform solution state but also in a form supported to a carrier or in the form of an insoluble particle of a carrier, the preparation of a polyolefin according to the present invention can be achieved by liquid-phase, slurry-phase, bulk-phase, or gas-phase polymerization. Further, the conditions for each polymerization reaction may be variously modified depending on the state of the catalyst composition used (homogeneous or heterogeneous such as the supported form), polymerization method (solution polymerization, slurry polymerization, or gas-phase polymerization), and/or desired polymerization results or forms of polymers. The degree of the modification can be easily determined by those skilled in the art. For example, when the polymerization is performed in a liquid phase or slurry phase, a separate solvent may be used or the olefin itself may be used as a medium. For the solvent, propane, butane, pentane, hexane, octane, decane, dodecane, cyclopentane, meth ylcyclopentane, cyclohexane, methylcyclohexane, benzene, toluene, xylene, dichloromethane, chloroethane, dichloroethane, chlorobenzene, etc., may be used alone, or two or more types thereof may be mixed at a certain ratio and used.

Examples of olefin monomers that can be used in the preparation method according to the present invention include ethylene, alpha-olefins, cycloolefins, etc., and diene olefins, triene olefins, and styrene olefins can also be used. The alpha-olefins include $C_{3-12}$, for example, $C_{3-8}$ aliphatic olefins, and specifically include propylene, 1-butene, 1-hexene, 1-heptene, 1-octene, 1-decene, 1-dodecene, 1-tetradecene, 1-hexadecene, 1-octadecene, 1-eicosene, 4-methyl-1-pentene, 3-methyl-1-pentene, 3-methyl-1-butene, 4,4-dimethyl-1-pentene, 4,4-diethyl-1-hexene, 3,4-dimethyl-1-hexene, etc. The cycloolefins include $C_{3-24}$, for example, $C_{4-18}$ cyclic olefins, and specifically include vinylcyclohexane, vinylcycloheptane, cyclopentene, cycloheptene, cyclobutene, cyclohexene, 3-methylcyclohexene, cyclooctene, tetracyclodecene, octacyclodecene, dicyclopentadiene, norbornene, 5-methyl-norbornene, 5-ethyl-2-norbornene, 5-isobutyl-2-norbornene, 5,6-dimethyl-2-norbornene, 5,5,6-trimethyl-2-norbornene, ethylene-norbornene-tetracyclododecene, etc. The diene olefins and triene olefins include $C_{4-26}$ polyenes containing two or three double bonds, and specifically include isoprene, 1,3-butadiene, 1,4-pentadiene, 1,4-hexadiene, 1,5-hexadiene, 1,9-decadiene, 2-methyl-1,3-butadiene, cyclopentadiene, etc. The styrene olefins include styrene or $C_{1-10}$ alkyl, alkoxy or halogenated alkyl, and styrene substituted with halogen, amine, silyl, etc., and specifically styrene, p-methylstyrene, allylbenzene, divinylbenzene, etc.

In the copolymerization of ethylene or propylene as olefin monomers with other alpha-olefins, the amount of alpha-olefins besides ethylene or propylene may be 90% or less of the total monomers. Conventionally, in the case of copolymers with ethylene, the amount of alpha-olefins may be 40 mol % or less, for example, 30 mol % or less, and preferably 20 mol % or less, and in the case of copolymers with propylene, 1 mol % to 90 mol %, preferably 5 mol % to 90 mol %, and more preferably 10 mol % to 70 mol %, but is not limited thereto. Further, alpha-olefins may be copolymerized with cycloolefins, and in particular, the amount of cycloolefins may be in a range of 1 mol % to 50 mol %, for example, 2 mol % to 50 mol %, based on the total amount of the copolymer.

In the method for preparing a polyolefin according to the present invention, the olefin monomer may be used alone or in combination of two or more types. Preferably, at least one compound selected from the group consisting of ethylene, propylene, 1-butene, 1-hexene, 1-octene, and 1-decene can be used, but the present invention is not limited thereto.

In addition, the olefin monomer may be homopolymerized, or two or more types of olefin monomers or polymers thereof may be alternated, or random- or block-copolymerized.

In the method for preparing a polyolefin according to the present invention, the amount of the catalyst composition is not particularly limited. For example, in the polymerized reaction system, the central metal concentration of the Group 4 transition metal compound of the present invention may be adjusted to be in a range of $1 \times 10^{-5}$ mol/L to $9 \times 10^{-5}$ mol/L and be used. Further, during polymerization reaction, the temperature and pressure are variable depending on the types of reactants and reaction conditions, etc. and thus are not particularly limited, and it may be performed at a temperature of 0° C. to 200° C. For example, it may be performed at a temperature of 100° C. to 180° C., and in the case of slurry or gas-phase polymerization, it may be performed at a temperature of 0° C. to 120° C., and more preferably, at 60° C. to 100° C. Meanwhile, polymerization pressure may be in a range of 1 bar to 150 bar, for example, 30 bar to 90 bar, and the pressure for polymerization may be controlled to the above range by the injection of an olefin monomer gas used in the reaction.

For example, the polymerization reaction can be performed batchwise, semi-continuously, or continuously. The polymerization reaction can also be performed through two or more steps having different reaction conditions, and the molecular weight of the finally obtained polymer can be adjusted by methods such as changing the polymerization temperature or injecting hydrogen into the reactor, etc.

Since the Group 4 transition metal compound of the present invention exhibits an excellent catalytic activity in polyolefin synthesis reactions, as well as having excellent thermal stability, it can be used for polyolefin synthesis reactions at high temperatures, and by changing the type of a central metal and ligand, the weight average molecular weight of synthesized polyolefins and the octene content in the polymer can be controlled. Therefore, it can be effectively used in polyolefin synthesis processes in which grades are controlled.

EXAMPLES

Hereinafter, the present invention will be described in more detail with reference to the following exemplary embodiments. However, these exemplary embodiments are for explaining the present invention in more detail, and the scope of the invention is not intended to be limited by these exemplary embodiments.

Preparation Example 1: Synthesis of Compound Represented by Formula 1-1 Comprising Zirconium as Central Metal

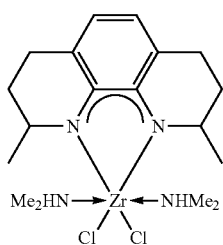

[Formula 1-1]

2,9-dimethyl-1,2,3,4,7,8,9,10-octahydro-1,10-phenanthroline (0.046 g, 0.21 mmol) and $Zr(NMe_2)_2Cl_2(dme)$ (0.073 mg, 0.21 mmol), which were each dissolved in 0.5 mL of toluene, were mixed. After stirring for 30 minutes, the solvent was removed using a vacuum pump, and the title compound was obtained.

$^1H$ NMR ($C_6D_6$): δ=6.49 (s, 2H, 5-phenanthrolin, 6-phenanthrolin), 5.02-4.94 (m, 2H, NCH), 3.00-2.85 (m, 2H, NH), 2.80-2.68 (m, 2H, 4-phenanthrolin, 7-phenanthrolin), 2.52-2.39 (m, 2H, 4-phenanthrolin, 7-phenanthrolin), 2.32 (dd, J=2.0, 6.4 Hz, 12H, $NH(CH_3)_2$), 1.58-1.50 (m, 4H, 3-phenanthrolin, 8-phenanthrolin), 1.24 (d, J=6.4 Hz, 6H, $CH_3$);

$^{13}C\{^1H\}$ NMR ($C_6D_6$): δ=141.60, 119.94, 116.95, 54.30, 41.80, 41.36, 28.97, 22.58, 22.11 ppm.

Preparation Example 2: Synthesis of Compound Represented by Formula 1-2 Comprising Zirconium as Central Metal

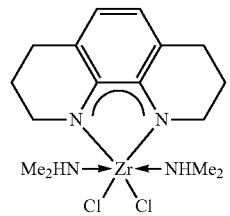

[Formula 1-2]

The title compound was obtained by the same conditions and methods as in Preparation Example 1, except that 1,2,3,4,7,8,9,10-octahydro-1,10-phenanthroline (0.043 g, 0.23 mmol) was used instead of 2,9-dimethyl-1,2,3,4,7,8,9,10-octahydro-1,10-phenanthroline.

$^1H$ NMR ($C_6D_6$): δ=6.42 (s, 2H, 5-phenanthroline, 6-phenanthrolin), 4.34-4.24 (m, 4H, 2-phenanthrolin, 9-phenanthrolin), 2.72-2.61 (m, 2H, NH), 2.56 (t, J=6.4 Hz, 4H, 4-phenanthrolin, 7-phenanthrolin), 2.29 (d, J=6.4 Hz, 12H, $NH(CH_3)_2$), 1.68-1.58 (m, 4H, 3-phenanthrolin, 8-phenanthrolin);

$^{13}C\{^1H\}$ NMR ($C_6D_6$): δ=142.19, 120.36, 118.10, 52.74, 41.13, 28.02, 24.62 ppm.

Preparation Example 3: Synthesis of Compound Represented by Formula 1-3 Comprising Zirconium as Central Metal The title compound was obtained by the same conditions and methods as in Preparation Example 1, except that 2,9-diisopropyl-1,2,3,4,7,8,9,10-octahydro-1,10-phenanthroline (0.068 g, 0.25 mmol) was used instead of 2,9-dimethyl-1,2,3,4,7,8,9,10-octahydro-1,10-phenanthroline.

$^1H$ NMR ($C_6D_6$): δ=6.44 (s, 2H, 5-phenanthrolin, 6-phenanthrolin), 4.72-4.60 (m, 2H, NCH), 3.18-3.00 (m, 2H, NH), 2.78-2.62 (m, 2H, 4-phenanthrolin, 7-phenanthrolin), 2.53-2.41 (m, 4H, 3-phenanthrolin, 4-phenanthrolin, 7-phenanthrolin, 8-phenanthrolin), 2.44 (d, J=7.2 Hz, 6H, $NH(CH_3)_2$), 2.42 (d, J=6.0 Hz, 6H, $NH(CH_3)_2$), 2.10-1.93 (m, 2H, 3-phenanthrolin, 8-phenanthrolin), 1.58-1.45 (m, 2H, CH), 1.13 (d, J=6.2 Hz, 6H, $CH_3$), 0.91 (d, J=7.2 Hz, 6H, $CH_3$);

$^{13}C\{^1H\}$ NMR ($C_6D_6$): δ=142.39, 120.04, 117.18, 62.94, 41.97, 35.79, 24.65, 23.60, 20.87, 19.22 ppm.

Preparation Example 4: Synthesis of Compound Represented by Formula 1-4 Comprising Zirconium as Central Metal

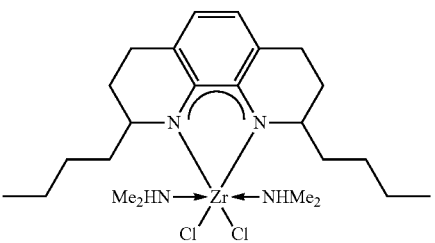

[Formula 1-4]

The title compound was obtained by the same conditions and methods as in Preparation Example 1, except that 2,9-di-n-butyl-1,2,3,4,7,8,9,10-octahydro-1,10-phenanthroline (0.053 g, 0.18 mmol) was used instead of 2,9-dimethyl-1,2,3,4,7,8,9,10-octahydro-1,10-phenanthroline. The reaction was carried out for 12 hours.

$^1$H NMR (C$_6$D$_6$): δ=6.51 (s, 2H, 5-phenanthrolin, 6-phenanthrolin), 4.88-4.75 (m, 2H, NCH), 3.05-2.89 (m, 2H, NH), 2.75-2.62 (m, 2H, 4-phenanthrolin, 7-phenanthrolin), 2.52-2.42 (m, 2H, 4-phenanthrolin, 7-phenanthrolin), 2.36 (dd, J=6.2, 15 Hz, 12H, NH(CH$_3$)$_2$), 1.92-1.80 (m, 4H, 3-phenanthrolin, 8-phenanthrolin), 1.62-1.28 (m, 12H, CH$_2$), 1.00 (t, J=7.0 Hz, 6H, CH$_3$);

$^{13}$C{$^1$H} NMR (C$_6$D$_6$): δ=141.92, 119.81, 117.03, 58.81, 41.93, 41.40, 35.01, 28.92, 24.47, 23.60, 22.44, 14.85 ppm.

Preparation Example 5: Synthesis of Compound Represented by Formula 1-8 Comprising Zirconium as Central Metal

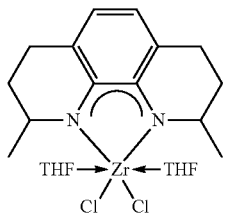

[Formula 1-8]

2,9-dimethyl-1,2,3,4,7,8,9,10-octahydro-1,10-phenanthroline (0.044 g, 0.21 mmol) and Zr(CH$_2$Ph)$_2$Cl$_2$(Et$_2$O)$_{0.2}$ (0.074 mg, 0.21 mmol) were dissolved in 1.0 mL of toluene, and a small amount of THF was added to dissolve. After stirring for 1 hour, the solvent was removed using a vacuum pump, and the title compound was obtained.

$^1$H NMR (C$_6$D$_6$): δ=1.65 (s, 2H, 5-phenanthrolin, 6-phenanthrolin), 5.50-5.40 (m, 2H, NCH), 4.32-4.16 (br, 8H, THF), 3.02-2.88 (m, 2H, 4-phenanthrolin, 7-phenanthrolin), 2.72-2.60 (m, 2H, 4-phenanthrolin, 7-phenanthrolin), 1.82-1.70 (m, 4H, 3-phenanthrolin, 8-phenanthrolin), 1.42 (d, J=6.8 Hz, 6H, CH$_3$), 1.34-1.20 (br, 8H, THF);

$^{13}$C{$^1$H} NMR (C$_6$D$_6$): δ=141.32, 119.52, 116.81, 76.31, 54.10, 29.23, 25.55, 22.66, 22.23 ppm.

Preparation Example 6: Synthesis of Compound Represented by Formula 1-9 Comprising Zirconium as Central Metal

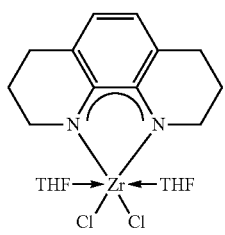

[Formula 1-9]

The title compound was obtained by the same conditions and methods as in Preparation Example 5, except that 1,2,3,4,7,8,9,10-octahydro-1,10-phenanthroline (0.042 g, 0.22 mmol) was used instead of 2,9-dimethyl-1,2,3,4,7,8,9,10-octahydro-1,10-phenanthroline.

$^1$H NMR (C$_6$D$_6$): δ=6.49 (s, 2H, 5-phenanthrolin, 6-phenanthrolin), 4.68-4.50 (m, 4H, NCH), 4.17 (br, 8H, THF), 2.75-2.60 (m, 4H, 4-phenanthrolin, 7-phenanthrolin), 1.80-1.70 (m, 4H, 3-phenanthrolin, 8-phenanthrolin), 1.18 (br, 8H, THF);

$^{13}$C{$^1$H} NMR (C$_6$D$_6$): δ=142.60, 119.76, 117.95, 75.91, 52.74, 28.15, 25.69, 25.19 ppm.

Preparation Example 7: Synthesis of Compound Represented by Formula 1-10 Comprising Zirconium as Central Metal

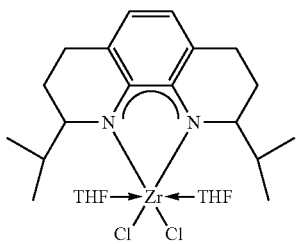

[Formula 1-10]

2,9-diisopropyl-1,2,3,4,7,8,9,10-octahydro-1,10-phenanthroline (0.047 g, 0.17 mmol) and Zr(CH$_2$Ph)$_2$Cl$_2$(Et$_2$O)$_{0.2}$ (0.080 mg, 0.22 mmol) were dissolved in 1.0 mL of toluene, and a small amount of THF was added to dissolve. Since Zr(CH$_2$Ph)$_2$Cl$_2$(Et$_2$O)$_{0.2}$ is unstable at room temperature, an excess amount of 1.3 equivalents thereof was used. After stirring for 1 hour, the solvent was removed using a vacuum pump, and after dissolving in toluene again, the excess Zr(CH$_2$Ph)$_2$Cl$_2$(Et$_2$O)$_{0.2}$ was filtered. Thereafter, the solvent was removed using a vacuum pump, and the title compound was obtained.

$^1$H NMR (C$_6$D$_6$): δ=6.56 (s, 2H, 5-phenanthrolin, 6-phenanthrolin), 5.22-5.10 (m, 2H, NCH), 4.31-4.12 (br, 8H, THF), 2.87-2.74 (m, 2H, 4-phenanthrolin, 7-phenanthrolin), 2.61-2.50 (m, 2H, 4-phenanthrolin, 7-phenanthrolin), 2.01-1.91 (m, 2H, 3-phenanthrolin, 8-phenanthrolin), 1.91-1.80 (m, 2H, 3-phenanthrolin, 8-phenanthrolin), 1.69-1.54 (m, 4H, CH$_2$), 1.54-1.34 (m, 8H, CH$_2$), 1.34-1.18 (br, 8H, THF), 0.99 (t, J=7.0 Hz, 6H, CH$_3$);

$^{13}$C{$^1$H} NMR (C$_6$D$_6$): δ=141.54, 119.48, 116.94, 76.36, 58.66, 35.21, 28.88, 25.65, 25.13, 23.84, 22.51, 14.79 ppm.

Preparation Example 8: Synthesis of Compound Represented by Formula 1-11 Comprising Zirconium as Central Metal

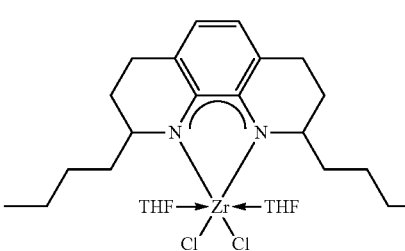

[Formula 1-11]

The title compound was obtained by the same conditions and methods as in Preparation Example 7, except that 2,9-di-n-butyl-1,2,3,4,7,8,9,10-octahydro-1,10-phenanthroline (0.050 g, 0.17 mmol) was used instead of 2,9-diisopropyl-1,2,3,4,7,8,9,10-octahydro-1,10-phenanthroline.

$^1$H NMR (C$_6$D$_6$): δ=6.52 (s, 2H, 5-phenanthrolin, 6-phenanthrolin), 4.92-2.82 (m, 2H, NCH), 4.39-4.08 (br, 8H, THF), 2.89 (m, 2H, 4-phenanthrolin, 7-phenanthrolin), 2.60-2.50 (m, 2H, 4-phenanthrolin, 7-phenanthrolin), 2.40-2.28 (m, 2H, 3-phenanthrolin, 8-phenanthrolin), 2.12-2.02 (m, 2H, 3-phenanthrolin, 8-phenanthrolin), 1.67-1.55 (m, 2H, CH), 1.33-1.18 (br, 8H, THF), 1.22 (d, J=6.8 Hz, 6H, CH$_3$), 1.02 (d, J=6.8 Hz, 6H, CH$_3$);
$^{13}$C{$^1$H} NMR (C$_6$D$_6$): δ=141.96, 119.63, 116.98, 76.49, 63.29, 34.54, 25.62, 24.45, 24.15, 21.42, 19.94 ppm.

Examples 1 to 8: Synthesis of Ethylene and 1-Octene Copolymer

A solution (1.0 M, 1-octene 4.0 g, 30 mL), in which 1-octene was dissolved in methylcyclohexane as a comonomer, and a methylaluminoxane solution (scavenger, 7% Al toluene solution, 29 mg, 75 mmol Al) as a cocatalyst to remove water and oxygen were added to a high-pressure polymerization reactor in a dry box, and the temperature of the high-pressure polymerization reactor was elevated to 100° C. outside the dry box. The transition metal compound (1.0 mmol) prepared in each of Preparation Examples 1 to 8 was dissolved in toluene, and methyldioctadecylammonium tetrakis(pentafluorophenyl)borate ([HNMe(C$_{18}$H$_{37}$)$_2$]$^+$[B(C$_6$F$_5$)$_4$]$^-$, 1.2 mmol) and a methylaluminoxane solution (7% Al toluene solution, 19 mg, 50 mmol Al, Al/Hf or Zr=125) were added in sequence. Toluene was further added to the reaction mixture to make a final solution volume of 3 mL to prepare an activated catalyst composition. After injecting the catalyst composition into the high-pressure polymerization reactor using a syringe, ethylene was injected at a pressure of 435 psig in the temperature range shown in Table 1 below, and ethylene and 1-octene were polymerized for 3 minutes. Ethylene gas was vented, and 10 mL of methanol was added at 0° C. to finish the reaction. After filtering the formed white solid compound, it was dried in a vacuum oven at 150° C. for several hours to prepare a polyolefin, that is, an ethylene and 1-octene copolymer. The results of each experiment are shown in Table 1.

Property Evaluation (1) Activity unit: kg (polyolefin)/mmol (catalyst central metal).hr (2) 1-octene content (unit: mol %): the 1-octene content in the polyolefin obtained through $^1$H NMR spectral analysis (3) Weight average molecular weight (Mw, unit: g/mol): Measured using gel permeation chromatography (GPC) based on polystyrene.

(4) Melting temperature (T$_m$, unit: ° C.): Measured using a differential scanning calorimeter (DSC 2920) manufactured by TA Instruments. Specifically, after raising the temperature to 200° C., the temperature was maintained thereat for 5 minutes, then the temperature was lowered to 30° C., and the temperature was raised again to set the maximum peak of a DSC curve as the melting temperature. In particular, the rate of increasing and decreasing the temperature was 10° C./min, and the melting temperature was determined while the second temperature was rising.

As shown in Table 1 above, when a polyolefin was prepared using the catalyst composition comprising the Group 4 transition metal compound according to the present invention, it was confirmed that the resulting polyolefin exhibited a high activity even at a high temperature of 100° C. or higher. In particular, it was confirmed that the transition metal compound prepared according to Preparation Example 5 exhibited an excellent catalytic activity (Example 5). Meanwhile, the polyolefin synthesized using the transition metal compound prepared according to Preparation Example 7 as a catalyst showed a relatively high weight average molecular weight and also showed a high 1-octene content. It was confirmed that the molecular weight of the polyolefin produced from the above results can be adjusted (in the range of weight average molecular weight of 10,000 to 400,000) depending on the structure of the coordinated ligand and the type of the central metal of the transition metal compound contained in the catalyst composition used, and it was confirmed that the 1-octene content also varied within a certain range (2.89 mol % to 3.53 mol %).

Simple modifications and variations of the present invention can easily be made by those skilled in the art, and it is understood that such modifications and variations are included within the scope of the present invention.

TABLE 1

| Example | Catalyst | Temperature (° C.) | Yield (g) | Activity | [1-octene] (mol) | M$_w$ × 10$^{-3}$ | M$_w$/M$_n$ | T$_m$ (° C.) |
|---|---|---|---|---|---|---|---|---|
| 1 | Preparation Example 1 | 100-112 | 1.70 | 34 | 2.89 | 16,360 | 3.39 | 115 |
| 2 | Preparation Example 2 | 100-112 | 1.52 | 30 | 3.41 | 69,587 | 17.30 | 109/121 |
| 3 | Preparation Example 3 | 100-111 | 0.97 | 19 | — | 333,100 | 30.47 | 135 |
| 4 | Preparation Example 4 | 100-105 | 0.84 | 8 | — | 109,096 | 19.72 | 124/108 |
| 5 | Preparation Example 5 | 100-131-129 | 3.65 | 73 | 3.05 | 10,408 | 1.99 | 116 |
| 6 | Preparation Example 6 | 100-120 | 2.77 | 55 | 3.07 | 55,926 | 11.56 | 123/108 |
| 7 | Preparation Example 7 | 100-113 | 0.71 | 14 | 3.53 | 375,864 | 21.45 | 133 |
| 8 | Preparation Example 8 | 100-105-102 | 0.58 | 12 | — | 19,932 | 5.84 | 113/124 |

The invention claimed is:

1. A Group 4 transition metal compound represented by Formula 1 below:

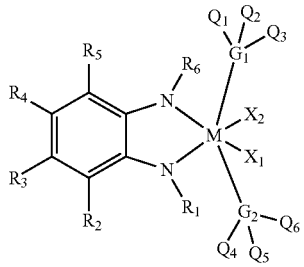

[Formula 1]

wherein, in Formula 1, M is a Group 4 transition metal of Ti, Zr, or Hf;

each of $X_1$ and $X_2$ is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene;

each of $R_1$ to $R_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or $R_2$ and $R_3$, or $R_4$ and $R_5$ are linked together to form a substituted or unsubstituted $C_{5-14}$ ring, or $R_1$ and $R_2$, or $R_5$ and $R_6$ are linked together to form a substituted or unsubstituted $C_{5-14}$ aliphatic ring, wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene;

each of $G_1$ and $G_2$ is independently an element of Group 5 or Group 6 of the Periodic Table; and each of $Q_1$ to $Q_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or any two of $Q_1$ to $Q_3$ or any two of $Q_4$ to $Q_6$ may be linked together to form a substituted or unsubstituted $C_{5-14}$ ring comprising or not comprising a heteroelement, with the proviso that, when $G_1$ is an element of Group 6 of the Periodic Table, then $Q_3$ is absent, and when $G_2$ is an element of Group 6 of the Periodic Table, then $Q_6$ is absent, wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

2. The Group 4 transition metal compound of claim 1, wherein the compound is represented by Formula 2 below:

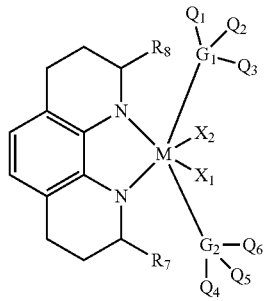

[Formula 2]

wherein, in Formula 2, each of $R_7$ and $R_8$ is independently hydrogen, or substituted or unsubstituted $C_{1-20}$ alkyl.

3. The Group 4 transition metal compound of claim 2, wherein each of $X_1$ and $X_2$ is independently halogen.

4. The Group 4 transition metal compound of claim 3, wherein $X_1$ and $X_2$ are both chlorine.

5. The Group 4 transition metal compound of claim 2, wherein each of $R_7$ and $R_8$ is identical to or different from each other, and is independently selected from the group consisting of hydrogen, methyl, ethyl, isopropyl, butyl, and phenyl.

6. The Group 4 transition metal compound of claim 2, wherein $G_1$ and $G_2$ are both nitrogen or both oxygen.

7. The Group 4 transition metal compound of claim 2, wherein each of $Q_1$, $Q_2$, $Q_4$ and $Q_5$ is independently hydrogen or methyl, and $Q_3$ or $Q_6$ is independently absent, hydrogen, or methyl.

8. The Group 4 transition metal compound according to claim 6, wherein:

i) when $G_1$ and $G_2$ are both nitrogen, and when any one of $Q_1$ to $Q_3$ is hydrogen and any one of $Q_4$ to $Q_6$ is hydrogen, the remaining two are both methyl, respectively, ii) when $G_1$ and $G_2$ are both oxygen, $Q_1$ and $Q_2$, and $Q_4$ and $Q_5$ are linked together to form a tetrahydrofuran ring by comprising the oxygen.

9. The Group 4 transition metal compound of claim 1, wherein the compound is selected from the group consisting of

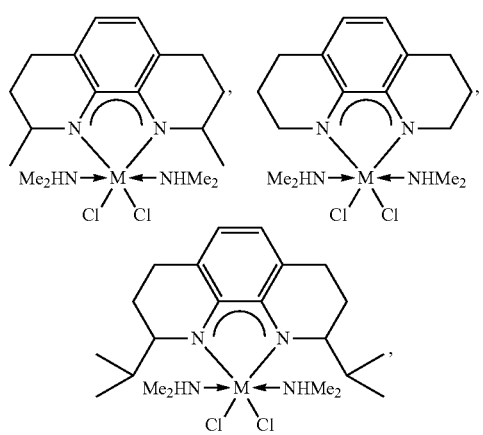

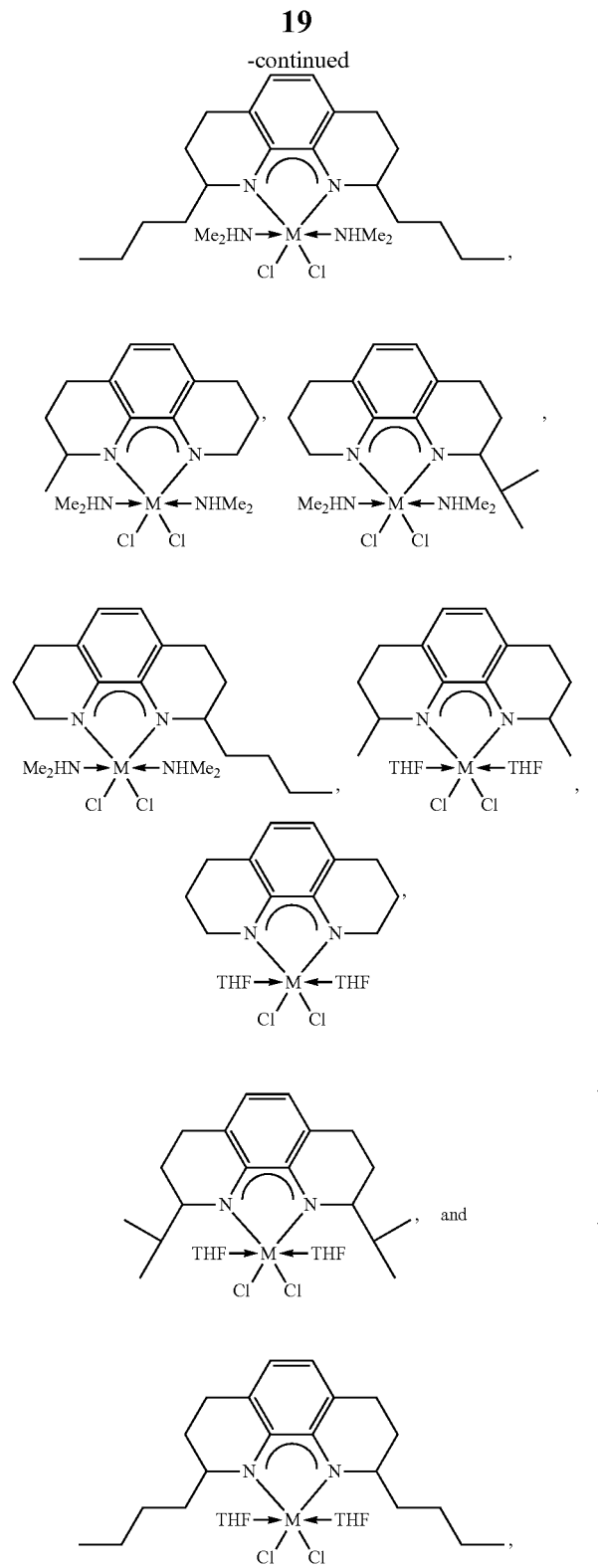

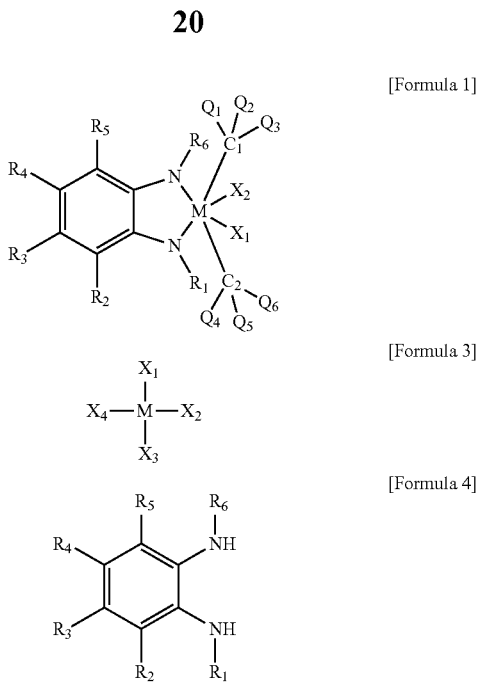

wherein, in the above formulas, M is a Group 4 transition metal of Ti, Zr, or Hf; Me is methyl; and THF is tetrahydrofuran.

10. A method for preparing a compound represented by Formula 1 below, comprising reacting a compound represented by Formula 3 below and a compound represented by Formula 4 below:

wherein, in the above formulae, M is a Group 4 transition metal of Ti, Zr, or Hf;

each of $X_1$, $X_2$ and $X_3$ is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene;

each of $R_1$ to $R_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or $R_2$ and $R_3$, or $R_4$ and $R_5$ are linked together to form a substituted or unsubstituted $C_{5-14}$ ring, or $R_1$ and $R_2$, or $R_5$ and $R_6$ are linked together to form a substituted or unsubstituted $C_{5-14}$ aliphatic ring, wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene;

each of $G_1$ and $G_2$ is independently an element of Group 5 or Group 6 of the Periodic Table; and each of $Q_1$ to $Q_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or any two of $Q_1$ to $Q_3$ or any two of $Q_4$ to $Q_6$ may be linked together to form a substituted or unsubstituted $C_{5-14}$ ring comprising or not comprising a heteroelement, with the proviso that, when $G_1$ is an element of Group 6 of the Periodic Table, then $Q_3$ is absent, and when $G_2$ is an element of Group 6 of the Periodic Table, then $Q_6$ is absent, wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene; and $X_4$ is halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

11. The method of claim 10, wherein the compound represented by Formula 4 is a 1,2,3,4,7,8,9,10-octahydro-1,10-phenanthroline derivative.

12. The method of claim 10, wherein the compound represented by Formula 3 and the compound represented by Formula 4 are reacted at an equivalent ratio of 1:0.9 to 1:1.5.

13. The method of claim 10, wherein a reaction is performed in a hydrocarbon solvent selected from the group consisting of $C_{5-10}$ aliphatic or aromatic hydrocarbon, $C_{1-10}$ saturated or unsaturated hydrocarbon unsubstituted or substituted with halogen atoms, and a mixture thereof.

14. The method of claim 10, wherein a reaction is performed at 0° C. to 100° C.

15. The method of claim 10, wherein a reaction is performed for 30 minutes to 30 hours.

16. A catalyst composition, comprising:
the Group 4 transition metal compound according to claim 1; and
at least one compound selected from the group consisting of a compound represented by Formula 5 below, a compound represented by Formula 6 below, and a compound represented by Formula 7 or Formula 8 below:

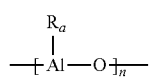

[Formula 5]

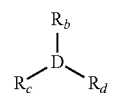

[Formula 6]

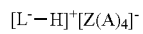

[Formula 7]

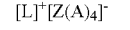

[Formula 8]

wherein, in the above formulas, $R_a$ is hydrogen, halogen, $C_{1-20}$ alkyl unsubstituted or substituted with halogen, $C_{3-20}$ cycloalkyl unsubstituted or substituted with halogen, $C_{6-40}$ aryl unsubstituted or substituted with halogen, or $C_{6-40}$ alkylaryl unsubstituted or substituted with halogen;

n is an integer of 2 or greater;

D is aluminum or boron;

each of $R_b$ to $R_d$ is identical to or different from each another, and is independently a hydrogen atom, halogen, $C_{1-20}$ alkyl unsubstituted or substituted with halogen, $C_{3-20}$ cycloalkyl unsubstituted or substituted with halogen, $C_{1-20}$ alkoxy, $C_{6-40}$ aryl unsubstituted or substituted with halogen, $C_{6-40}$ alkylaryl, or $C_{6-40}$ arylalkyl unsubstituted or substituted with halogen;

L is a neutral or cationic Lewis acid;

L' is a Lewis base;

Z is a Group 13 element; and

A is substituted or unsubstituted $C_{6-20}$ aryl; or substituted or unsubstituted $C_{1-20}$ alkyl.

17. The catalyst composition of claim 16, comprising:
a compound represented by Formula 5, a compound represented by Formula 6, or a mixture thereof; and
a compound represented by Formula 7 or Formula 8.

18. The catalyst composition of claim 17, comprising:
a compound represented by Formula 1;
a compound represented by Formula 5, a compound represented by Formula 6, or a mixture thereof; and
a compound represented by Formula 7 or Formula 8, at a molar ratio of 1:1 to 5:20 to 500.

19. A method for preparing a polyolefin, comprising performing a polymerization reaction of olefin monomers, in the presence of the catalyst composition according to claim 16.

20. The method of claim 19, wherein the olefin monomers are at least one compound selected from the group consisting of ethylene, propylene, 1-butene, 1-hexene, 1-octene, and 1-decene.

* * * * *